(12) United States Patent
Smith et al.

(10) Patent No.: US 9,758,781 B2
(45) Date of Patent: Sep. 12, 2017

(54) METHODS TO PREVENT AND TREAT AUTOSOMAL DOMINANT NON-SYNDROMIC HEARING LOSS

(71) Applicant: University of Iowa Research Foundation, Iowa City, IA (US)

(72) Inventors: Richard J. H. Smith, Iowa City, IA (US); Seiji Shibata, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/850,740

(22) Filed: Sep. 10, 2015

(65) Prior Publication Data

US 2016/0090597 A1 Mar. 31, 2016

Related U.S. Application Data

(60) Provisional application No. 62/057,678, filed on Sep. 30, 2014.

(51) Int. Cl.
| | |
|---|---|
| *A61K 48/00* | (2006.01) |
| *C12N 15/113* | (2010.01) |
| *C12Q 1/68* | (2006.01) |
| *A61K 31/713* | (2006.01) |
| *A61K 31/00* | (2006.01) |

(52) U.S. Cl.
CPC ............ *C12N 15/113* (2013.01); *A61K 31/00* (2013.01); *A61K 31/713* (2013.01); *C12Q 1/6883* (2013.01); *C12N 2310/141* (2013.01); *C12N 2320/30* (2013.01); *C12Q 2600/156* (2013.01)

(58) Field of Classification Search
CPC .................................................... A61K 48/00
See application file for complete search history.

(56) References Cited

U.S. PATENT DOCUMENTS

| | | |
|---|---|---|
| 4,962,091 A | 10/1990 | Eppstein et al. |
| 5,350,674 A | 9/1994 | Boenisch et al. |
| 5,585,362 A | 12/1996 | Wilson et al. |

FOREIGN PATENT DOCUMENTS

| | | |
|---|---|---|
| WO | 9407529 | 4/1994 |

OTHER PUBLICATIONS

Hilgert et al. (Mutation Research 681m 2009: 189-196).*
Azaiez, et al., "TBC1D24 mutation causes autosomal-dominant nonsyndromic hearing loss", Hum Mutat 35 (7), 819-823 (2014).
Boudreau, et al., "Generation of hairpin-based RNAi vectors for biological and therapeutic application", Methods Enzymol. 507, 275-296 (2012).
Boudreau, et al., "Rational design of therapeutic siRNAs: Minimizing off-targeting potential to improve the safety of RNAi therapy for Huntington's disease", Molecular Therapy vol. 19 (12), 2169-2177 (2011).
Shibata, et al., "RNA Interference Prevents Autosomal-Dominant Hearing Loss", The American Journal of Human Genetic 98, 1101-1113 (2016).
Zhao, et al., "A novel DFNA36 mutation in TMC1 orthologous to the Beethoven (Bth) mouse associated with autosomal dominant hearing loss in a Chinese family", PLOS One, vol. 9 (5), e97064 1-9 (2014).

* cited by examiner

*Primary Examiner* — Kimberly Chong
(74) *Attorney, Agent, or Firm* — Viksnins Harris Padys Malen LLP

(57) ABSTRACT

The present invention provides in certain embodiments a method of treating autosomal dominant non-syndromic hearing loss (ADNSHL) in a patient in need thereof comprising: (a) identifying a mutation in an ADNSHL-causing gene, (b) preparing a ADNSHL therapeutic miRNA, and (c) administering to the patient a pharmaceutical composition comprising the ADNSHL therapeutic miRNA and a pharmaceutically acceptable carrier.

20 Claims, 15 Drawing Sheets

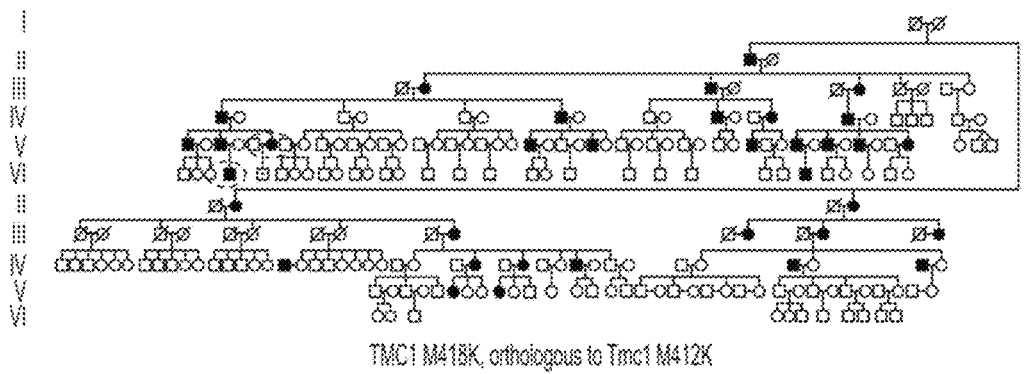
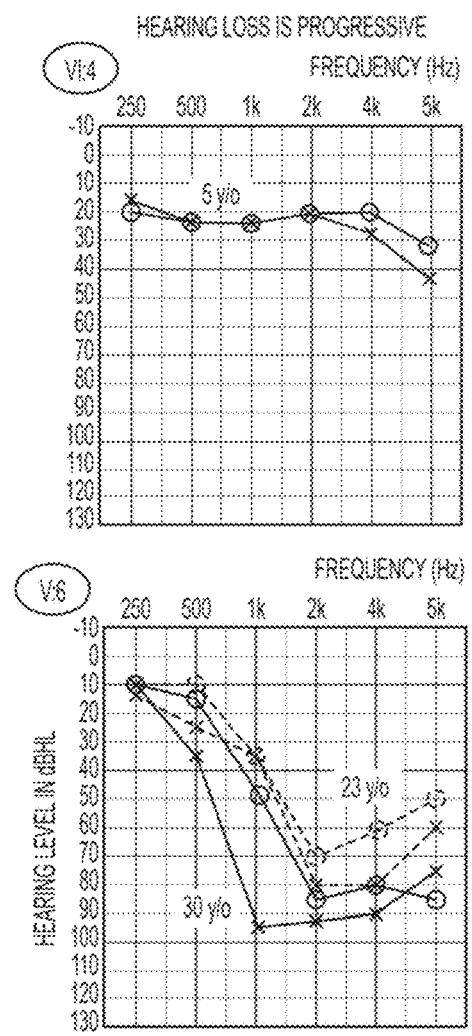
Figure 3

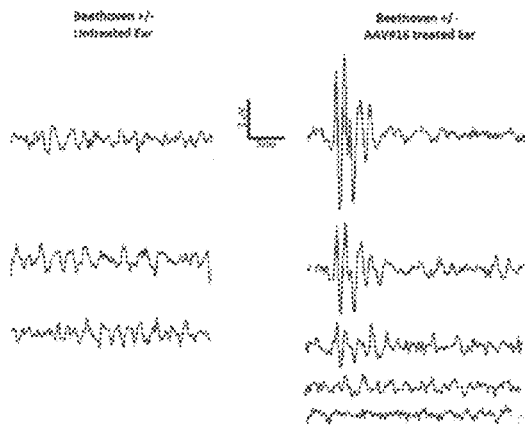
FIG. 12A
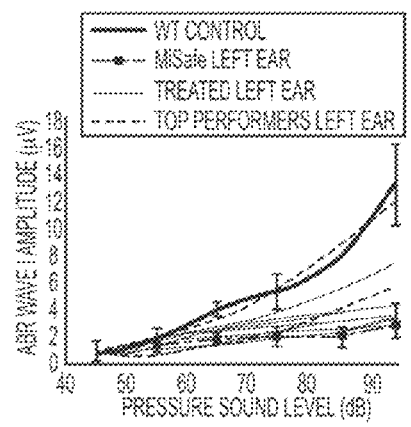
FIG. 12B
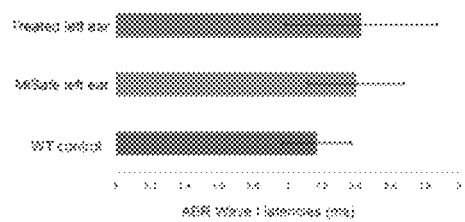
FIG. 12C
FIG. 12D
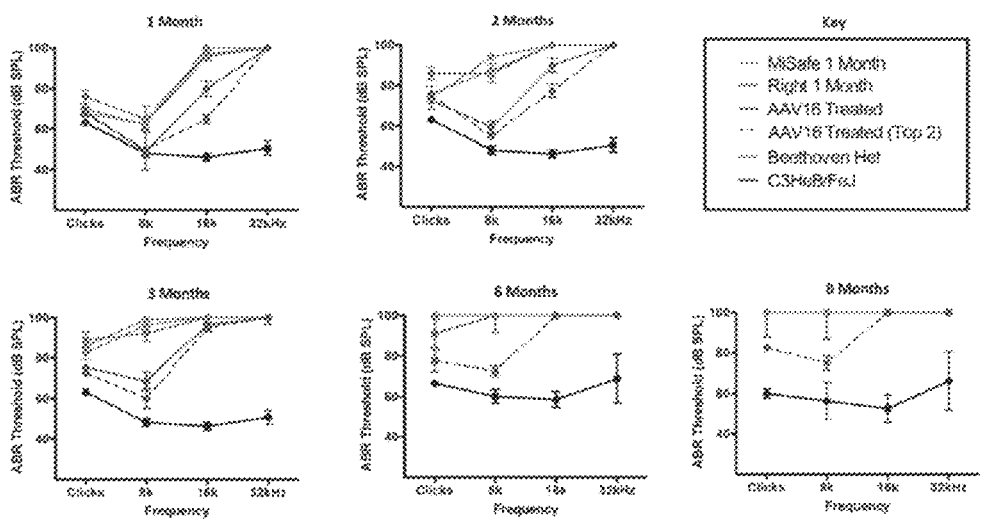
Figure 12

FIG.14A
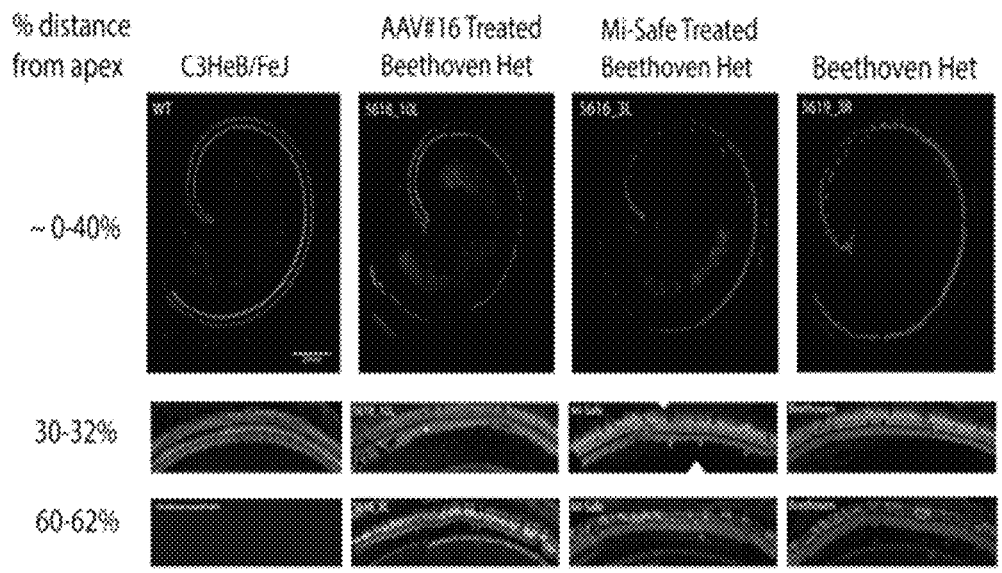
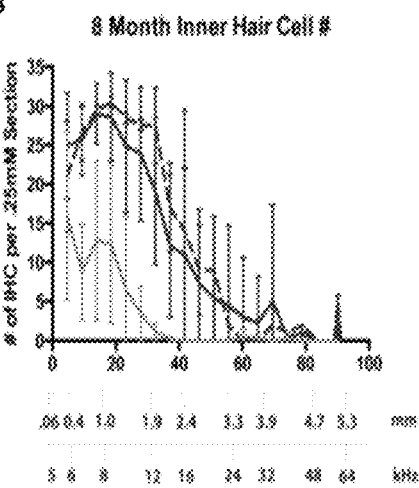
FIG.14B
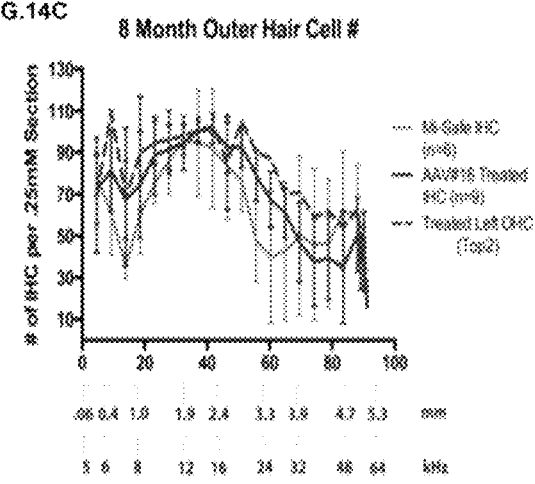
FIG.14C

METHODS TO PREVENT AND TREAT AUTOSOMAL DOMINANT NON-SYNDROMIC HEARING LOSS

RELATED APPLICATION

This application claims the benefit of priority of U.S. Provisional Application Ser. No. 62/057,678 filed on Sep. 30, 2014, which application is herein incorporated by reference.

GOVERNMENT FUNDING

This invention was made with government support under R01 DC003544 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 16, 2015, is named 17023.157US1_SL.txt and is 3,846 bytes in size.

BACKGROUND OF THE INVENTION

Progressive hearing loss can generally be categorizd as conductive hearing loss, sensorineural hearing loss (SNHL), or mixed hearing loss. Conductive hearing loss occurs when hearing loss is due to problems with the ear canal, ear drum, or middle ear and its bones (the malleus, incus, and stapes). Sensorineural hearing loss (SNHL) occurs when hearing loss is due to problems of the inner ear, also known as nerve-related hearing loss. Mixed hearing loss refers to a combination of conductive and sensorineural hearing loss, where there may be damage in the outer or middle ear and in the inner ear (cochlea) or auditory nerve.

"Nonsyndromic deafness" is hearing loss that is not associated with other signs and symptoms. In contrast, "syndromic deafness" involves hearing loss that occurs with abnormalities in other parts of the body. Different types of nonsyndromic deafness are generally named according to their inheritance patterns. Nonsyndromic deafness can occur at any age. About 1 in 1,000 children in the United States is born with profound deafness, and another 2 to 3 per 1,000 children are born with partial hearing loss. More than half of these cases are caused by genetic factors. Most cases of genetic deafness (70 to 80%) are nonsyndromic and the remaining cases are caused by specific genetic syndromes.

Researchers have identified more than 70 genes that, when altered, are associated with nonsyndromic deafness; however, some of these genes have not been fully characterized. Many genes related to deafness are involved in the development and function of the inner ear. Mutations in these genes contribute to hearing loss by interfering with critical steps in processing sound. Different mutations in the same gene can be associated with different types of hearing loss, and some genes are associated with both syndromic and nonsyndromic deafness. Nonsyndromic deafness can have different patterns of inheritance. 20% to 25% of nonsyndromic deafness cases are autosomal dominant (i.e., one copy of the altered gene in each cell is sufficient to result in hearing loss).

Current treatments for hearing loss include the use of hearing aids, cochlear implants and brainstem implants. Both hearing aids and cochlear implants amplify sounds to enable deaf people to hear, to distinguish environmental sounds and warning signals, and to modulate the voice and make speech more intelligible. Brain stem implants help persons who have had both acoustic nerves destroyed (e.g., by bilateral temporal bone fractures or neurofibromatosis) have some sound perception restored by means of electrodes connected to from sound-detecting and sound-processing devices directly to the brain stem. Currently, there is a need for effective treatments to mitigate progressive autosomal dominant non-syndromic hearing loss (ADNSHL).

SUMMARY OF THE INVENTION

The present invention provides in certain embodiments a method of treating autosomal dominant non-syndromic hearing loss (ADNSHL) in a patient in need thereof comprising: (a) identifying a mutation in an ADNSHL-causing gene, wherein the mutation causes ADNSHL in the patient; (b) preparing a ADNSHL therapeutic miRNA, wherein the ADNSHL therapeutic miRNA is of 18 to 25 nucleotides in length and suppresses expression of the ADNSHL-causing gene to a greater level than it suppresses expression of the corresponding wild-type (non-mutated) gene; and (c) administering to the patient a pharmaceutical composition comprising the ADNSHL therapeutic miRNA and a pharmaceutically acceptable carrier.

A method of treating autosomal dominant non-syndromic hearing loss (ADNSHL) in a patient in need thereof comprising administering to a patient identified as having a mutation in an ADNSHL-causing gene a pharmaceutical composition comprising pharmaceutically acceptable carrier and a ADNSHL therapeutic miRNA, wherein the miRNA is of 18 to 25 nucleotides in length and knocks-down the ADNSHL-causing gene function at a higher level than it knocks-down gene function in a corresponding wild-type gene.

BRIEF DESCRIPTION OF THE FIGURES

FIG. 3. The TMC1 M418K mutation in humans is orthologous to the murine Tmc1 M412K mutation. A large family segregating this mutation is shown. In persons carrying this mutation, over a two decade time span, hearing loss progresses as is evident by an audiogram from a mutation carrier at the age of 5 years (top right) and audiograms from a mutation carrier at the age of 23 and 30 years (bottom right). Note the progression in hearing loss.

FIGS. 12A-D. Pure tone ABR thresholds. FIG. 12A) Representative ABR traces of the untreated right ear and the treated left ear in Bth/+miTmc mice at 3 months. 8 kHz pure tone bursts were used to evoke responses at 95, 85, 75, 65 and 60 dB SPL (top to bottom). FIG. 12B) 8k ABR wave I amplitudes at 1 month. Each blue line represents the wave I amplitude measured from peak to nadir for one animal in the Bth/+miTmc cohort. Black and orange lines are means for C3HeB/FeJ and Bth/+miSafe treated animals, respectively. FIG. 12C) ABR wave I latencies for left ears of Bth/+miTmc mice, Bth/+miSafe mice, and C3HeB/FeJ control mice. FIG. 12D) Pure tone ABR thresholds collected at 1, 2, 3, 6 and 8 months. Data were collected for each of the groups being followed: background (C3HeB/FeJ), Bth/+, Bth/+miTmc and Bth/+miSafe animals; data graphed are means with error bars representing ±standard error of the mean (SEM).

FIGS. 14A-C. 8-month hair cell survival. FIG. 14A) Immunofluorescence images labeled with Myo7a and phalloidin to show hair cells and filamentous actin, respectively. The top, middle and bottom panels show representative cochlear whole mounts in each of the four groups of animals at the apical turn, 30-32% distance from the apex, and 60-62% distance from the apex, respectively. FIGS. 14B, 14C) Number of surviving IHCs (B) or OHCs (C) at 8 months measured in 0.25 mm segments from the apex to the base of the cochlea. Lines represent the mean number of surviving hair cells in Bth/+miTmc (dark) or Bth/+miSafe (light) animals. Error bars show ±standard deviation. The frequency corresponding to each physical position in the mouse cochlea is shown in kHz below the x-axis.

FIG. 15A) Shown are 8 families of transduction currents under the conditions labeled at the top. The top row shows the largest families of currents encountered for each condition and the bottom row shows the smallest. FIG. 15B) Maximal transduction currents were recorded for 74 hair cells. Each open circle represents current measured from a single cell (filled circles, mean for each group; horizontal line, median; box top and bottom, S.E.; error bars, S.D.; number of cells, shown at bottom).

DETAILED DESCRIPTION

Figure 1:
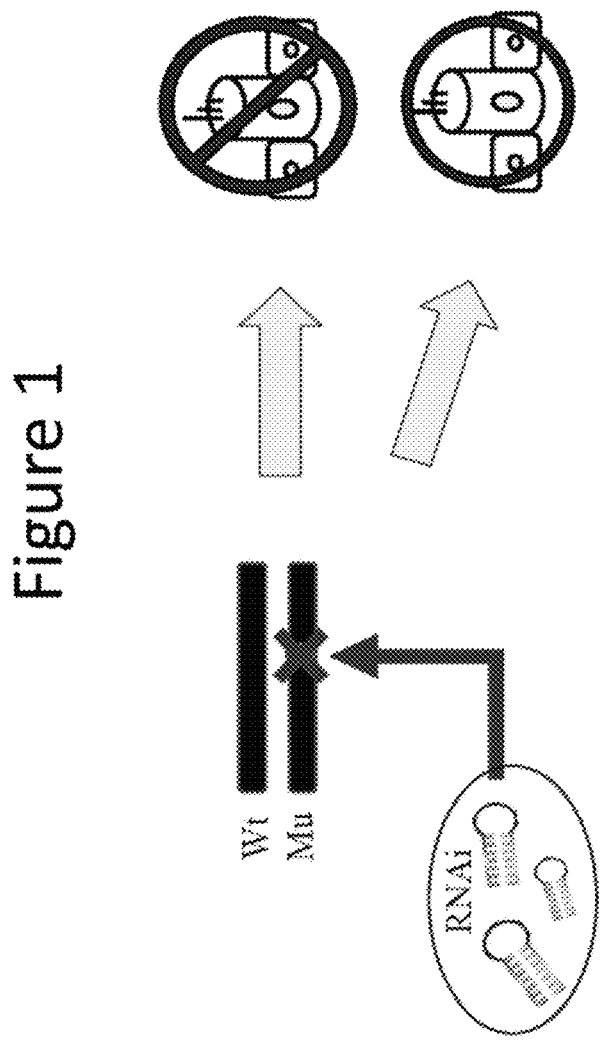
FIG. 1. Schematic overview of the overarching hypothesis showing knockdown (suppression) of the mutant (Mu) allele to preserve hair cells and hearing (bottom arrow). In the absence of knockdown, hair cells are damaged and hearing loss progresses (top arrow).

RNAi directs sequence-specific gene silencing by double-stranded RNA (dsRNA) which is processed into functional small inhibitory RNAs (~21nt). In nature, RNAi for regulation of gene expression occurs primarily via small RNAs known as microRNAs (miRNAs). Mature microRNAs (~19-25 nts) are processed from larger primary miRNA transcripts (pri-miRNAs) which contain stem-loop regions. Via a series of processing events catalyzed by the ribonucleases, Drosha and Dicer, the miRNA duplex region is liberated and a single strand (the antisense "guide" strand) is then incorporated into the RNA Induced Silencing Complex (RISC), thus generating a functional complex capable of base-pairing with and silencing target transcripts. The mode of target repression primarily depends upon the degree of complementarity; transcript cleavage typically requires a high-degree of base-pairing, whereas translational repression and mRNA destabilization occurs when small RNAs bind imperfectly to target transcripts (most often in the 3' UTR). Indeed for the latter, short stretches of complementarity—as little as 6 bp—may be sufficient to cause gene silencing.

Treatment of later-onset progressive hearing loss offers potential advantages relative to congenital hearing loss in that initially all cell types in the cochlea are present and functioning normally. Although the functional nature of many of the dominant mutations most often associated with progressive hearing loss has not been studied in detail, many appear to act as gain-of-function mutations. In such cases, targeted genetic therapies require selective inhibition of the mutant allele.

The present invention provides a method of treating a subject with autosomal dominant non-syndromic hearing loss (ADNSHL) by administering to the subject a nucleic acid, an expression cassette, a vector, or a composition as described herein so as to treat the ADNSHL.

The present invention provides in certain embodiments a method of treating autosomal dominant non-syndromic hearing loss (ADNSHL) in a patient in need thereof comprising: (a) identifying a mutation in an ADNSHL-causing gene, wherein the mutation causes ADNSHL in the patient; (b) preparing a ADNSHL therapeutic miRNA, wherein the ADNSHL therapeutic miRNA is of 18 to 25 nucleotides in length and knocks-down the ADNSHL-causing gene function at a higher level than it knocks-down gene function in a corresponding wild-type gene; (c) administering to the patient a pharmaceutical composition comprising the ADNSHL therapeutic miRNA and a pharmaceutically acceptable carrier.

In the clinical setting, to identify the specific ADNSHL gene and mutation, a comprehensive genetic panel of genes that causes non-syndromic deafness is screened using targeted genomic enrichment with massively parallel sequencing. Relevant to the heterogeneity of ADNSHL, nearly 75% of identified mutations will be novel—that is to say, a genetic change will be identified that has not been previously reported or described in the scientific literature.

Once a specific mutation has been identified, multiple miRNAs are made, each of which incorporates the identified mutation at a slightly different position in the miRNA structure. These miRNAs are tested to identify the specific miRNA that most potently knocks-down the ADNSHL-causing gene function while having minimal knock-down effect on the corresponding wild-type gene.

In certain embodiments, the ADNSHL-causing gene is ACTG1, CCDC50, CEACAM1, COCH, COL11A2, CRYM, DFNA5, DIABLO, DIAPH1, DSPP, EYA4, GJB2, GJB3, GJB6, GRHL2, HOMER2, KCNQ4, MYH14, MYH9, MYO1A, MYO6, P2RX, POU4F3, SLC1748, TBC1D24, TECTA, TJP2, TMC1, TNC, or WFS1.

In certain embodiments, the ADNSHL-causing gene is TMCJ. In certain embodiments, the ADNSHL-causing gene is TMC1 containing a missense mutation M4182K. The orthologous murine change is Tmc/M412K.

The present invention provides in certain embodiments a method of treating autosomal dominant non-syndromic hearing loss (ADNSHL) in a patient in need thereof comprising administering to a patient identified as having a missense mutation in TMC1 (M418K) a pharmaceutical composition comprising pharmaceutically acceptable carrier and a ADNSHL therapeutic miRNA, wherein the miRNA is of 18 to 25 nucleotides in length and knocks-down the TMC1 (M4128) gene function at a higher level than it knocks-down gene function in a corresponding wild-type TMC1 gene.

In certain embodiments, the therapeutic miRNA has at least 90% complementarity to any one of SEQ ID NO: 1-15.

In certain embodiments, the miRNA is of 20 to 22 nucleotides in length. In certain embodiments, the miRNA is 21 nucleotides in length.

In certain embodiments, the miRNA knocks-down the ADNSHL-causing gene function by at least 50% more than it knocks-down the corresponding wild-type gene function.

In certain embodiments, the pharmaceutical composition further comprises an shRNA or siRNA.

In certain embodiments, the miRNA is contained in an expression cassette comprising a promoter operably linked to a nucleic acid encoding the miRNA. In certain embodiments, the promoter is a polII or polIII promoter (such as an H1 or U6 promoter). In certain embodiments, the promoter is a tissue-specific promoter. In certain embodiments, the promoter is an inducible promoter.

In certain embodiments, the expression cassette further comprises a marker gene (such as green fluorescent protein (GFP)).

In certain embodiments, the expression cassette is contained in a vector.

In certain embodiments, the vector is an adeno-associated virus (AAV) vector, an adenovirus vector or a bovine AAV vector.

In certain embodiments, the pharmaceutical composition is administered intravenously and/or directly into the patient's inner ear.

The present invention provides a method of suppressing the accumulation of gene product from an ADNSHL-causing gene in a cell by introducing nucleic acid molecules (e.g., a ribonucleic acid (RNA)) described herein into the cell in an amount sufficient to suppress accumulation of the ADNSHL-causing gene product in the cell. In certain embodiments, the accumulation of gene product is suppressed by at least 10%. In certain embodiments, the accumulation of gene product is suppressed by at least 10%, 20%, 30%, 40%, 50%, 60%, 70%, 80%, 90% 95%, or 99%. In certain embodiments, the suppression of the accumulation of the protein is in an amount sufficient to cause a therapeutic effect, e.g., to reduce the ADNSHL.

The present invention provides a method to inhibit expression of an ADNSHL-causing gene in a cell by introducing a nucleic acid molecule (e.g., a ribonucleic acid (RNA)) described herein into the cell in an amount sufficient to inhibit expression of the ADNSHL-causing gene product, and wherein the RNA inhibits expression of the ADNSHL-causing gene. In certain embodiments, the ADNSHL-causing gene product is inhibited by at least 10%, 20%, 30%, 40%, 50%, 60%, 70%, 80%, 90% 95%, or 99%.

The present invention provides a viral vector comprising a promoter and a micro RNA (miRNA) specific for a target sequence. In certain embodiments, the promoter is an inducible promoter. In certain embodiments, the vector is an adenoviral, lentiviral, adeno-associated viral (AAV), poliovirus, HSV, or murine Maloney-based viral vector. In certain embodiments, the targeted sequence is a sequence associated with ADNSHL.

The present invention also provides a method to inhibit expression of a protein associated with ADNSHL in a mammal in need thereof, by introducing the vector encoding a miRNA described herein into a cell in an amount sufficient to inhibit expression of the ADNSHL-causing gene product. The ADNSHL-causing gene product is inhibited by at least 10%, 20%, 30%, 40%, 50%, 60%, 70%, 80%, 90% 95%, or 99%.

This invention relates to compounds, compositions, and methods useful for modulating ADNSHL gene expression using miRNA molecules. This invention also relates to compounds, compositions, and methods useful for modulating the expression and activity of other genes involved in pathways of ADNSHL gene expression and/or activity by RNA interference (RNAi) using small nucleic acid molecules. An "RNA interference" or "RNAi" molecule; "small interfering RNA," "short interfering RNA" or "siRNA"

molecule; "short hairpin RNA" or "shRNA" molecule; or "miRNA" molecule is a RNA duplex of nucleotides that is targeted to a nucleic acid sequence of interest. An "RNA duplex" refers to the structure formed by the complementary pairing between two regions of a RNA molecule. An RNAi molecule is "targeted" to a gene in that the nucleotide sequence of the duplex portion of the RNAi molecule is complementary to a nucleotide sequence of the targeted gene. In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24 or 25 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length. In particular, the instant invention features small nucleic acid molecules, such as short interfering nucleic acid (siNA), short interfering RNA (siRNA), double-stranded RNA (dsRNA), micro-RNA (miRNA), and short hairpin RNA (shRNA) molecules and methods used to modulate the expression of ADNSHL genes. An RNA molecule of the instant invention can be, e.g., chemically synthesized, expressed from a vector or enzymatically synthesized.

As used herein when a claim indicates an RNA "corresponding to" it is meant the RNA that has the same sequence as the DNA, except that uracil is substituted for thymine.

The present invention further provides a method of substantially silencing a target gene of interest or targeted allele for the gene of interest in order to provide a therapeutic effect. As used herein the term "substantially silencing" or "substantially silenced" refers to decreasing, reducing, or inhibiting the expression of the target gene or target allele by at least about 5%, 10%, 15%, 20%, 25%, 30%, 35%, 40%, 45%, 50%, 55%, 60%, 65%, 70%, 75%, 80%, 85% to 100%. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the condition. Therapeutic effects can be measured quantitatively by a physician or qualitatively by a patient afflicted with the hearing loss targeted by the miRNA. In certain embodiments wherein both the mutant and wild-type allele are substantially silenced, the term therapeutic effect defines a condition in which silencing of the wild-type allele's expression does not have a deleterious or harmful effect on normal functions such that the patient would not have a therapeutic effect.

In one embodiment, the invention features a method for treating or preventing ADNSHL in a subject or organism comprising contacting the subject or organism with an miRNA of the invention under conditions suitable to modulate the expression of the ADNSHL gene in the subject or organism whereby the treatment or prevention of ADNSHL can be achieved. The miRNA molecule of the invention can be expressed from vectors as described herein or otherwise known in the art to target appropriate tissues or cells in the subject or organism.

In one embodiment, the invention features a method for treating or preventing ADNSHL in a subject or organism comprising, contacting the subject or organism with an miRNA molecule of the invention via local administration to relevant tissues or cells, for example, by administration of vectors or expression cassettes of the invention that provide miRNA molecules of the invention to relevant cells.

Methods of delivery of viral vectors include, but are not limited to, intravenous administration and administration directly into a patient's inner ear. Generally, AAV virions may be introduced into cells using either in vivo or in vitro transduction techniques. If transduced in vitro, the desired recipient cell will be removed from the subject, transduced with AAV virions and reintroduced into the subject. Alternatively, syngeneic or xenogeneic cells can be used where those cells will not generate an inappropriate immune response in the subject.

In one embodiment, pharmaceutical compositions will comprise sufficient genetic material to produce a therapeutically effective amount of the miRNA of interest, i.e., an amount sufficient to reduce or ameliorate symptoms of the disease state in question or an amount sufficient to confer the desired benefit. The pharmaceutical compositions may also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

As is apparent to those skilled in the art in view of the teachings of this specification, an effective amount of viral vector which must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

It should be understood that more than one transgene could be expressed by the delivered viral vector. Alternatively, separate vectors, each expressing one or more different transgenes, can also be delivered as described herein. Furthermore, it is also intended that the viral vectors delivered by the methods of the present invention be combined with other suitable compositions and therapies.

The present invention further provides miRNA or shRNA, an expression cassette and/or a vector as described herein for use in medical treatment or diagnosis.

The present invention provides the use of an miRNA or shRNA, an expression cassette and/or a vector as described herein to prepare a medicament useful for treating ADNSHL.

The present invention also provides a nucleic acid, expression cassette, vector, or composition of the invention for use in therapy.

The present invention also provides a nucleic acid, expression cassette, vector, or composition of the invention for treating ADNSHL.

MicroRNA Shuttles for RNAi

Artificial miRNA shuttle vectors are used to mimic natural miRNAs and suppress the mutated ADNSHL gene of interest miRNA shuttles closely recapitulate natural miRNA structures, are predictably processed and are amenable to control by tissue-specific and/or regulated promoters. They are outstanding for long-term RNA interference studies to prevent progression of ADNHSL by suppressing expression of the mutated gene. miRNAs are small cellular RNAs (~22nt) that are processed from precursor stem loop transcripts. Known miRNA stem loops can be modified to contain RNAi sequences specific for genes of interest. miRNA molecules can be preferable over shRNA molecules because miRNAs are endogenously expressed. Therefore, miRNA molecules are unlikely to induce dsRNA-responsive interferon pathways, they are processed more efficiently than shRNAs, and they have been shown to silence 80% more effectively.

Treatment of ADNSHL

"Treating" as used herein refers to ameliorating at least one symptom of, curing and/or preventing the development of hearing loss. In certain embodiment of the invention, RNAi molecules are employed to inhibit expression of a target gene. By "inhibit expression" is meant to reduce, diminish or suppress expression of a target gene. Expression of a target gene may be inhibited via "gene silencing." Gene silencing refers to the suppression of gene expression, e.g., transgene, heterologous gene and/or endogenous gene expression, which may be mediated through processes that affect transcription and/or through processes that affect post-transcriptional mechanisms. In some embodiments, gene silencing occurs when an RNAi molecule initiates the inhibition or degradation of the mRNA transcribed from a gene of interest in a sequence-specific manner via RNA interference, thereby preventing translation of the gene's product.

Disclosed herein is a strategy that results in substantial silencing of targeted genes via RNAi. Use of this strategy results in markedly diminished in vitro and in vivo expression of targeted genes. This strategy is useful in reducing expression of targeted genes in order to provide therapy for ADNSHL. As used herein the term "substantial silencing" means that the mRNA of the targeted gene is inhibited and/or degraded by the presence of the introduced miRNA, such that expression of the targeted gene is reduced by about 10% to 100% as compared to the level of expression seen when the miRNA is not present. Generally, when an gene is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the miRNA is not present. As used herein the term "substantially normal activity" means the level of expression of a gene when an miRNA has not been introduced to a cell.

RNA Interference (RNAi) Molecules

An "RNA interference," "RNAi," "small interfering RNA" or "short interfering RNA" or "siRNA" or "short hairpin RNA" or "shRNA" molecule, or "miRNA" is a RNA duplex of nucleotides that is targeted to a nucleic acid sequence of interest, for example, an ADNSHL-causing gene. An "RNA duplex" refers to the structure formed by the complementary pairing between two regions of a RNA molecule. As used herein the term "miRNA" encompasses both the naturally occurring miRNA sequences as well as artificially generated miRNA shuttle vectors.

The miRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

"Knock-down," "knock-down technology" refers to a technique of gene silencing in which the expression of a target gene is reduced as compared to the gene expression prior to the introduction of the miRNA, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of protein may be reduced by 10, 20, 30, 40, 50, 60, 70, 80, 90, 95, or 99%. In some embodiments, the expression is reduced by about 90% (i.e., only about 10% of the amount of protein is observed a cell as compared to a cell where miRNA molecules have not been administered).

According to a method of the present invention, the expression of an ADNSHL-causing gene product can be modified via RNA interference. For example, the accumulation of a gene product can be suppressed in a cell. The term "suppressing" refers to the diminution, reduction or elimination in the number or amount of transcripts present in a particular cell. For example, the accumulation of mRNA encoding ADNSHL-causing gene product can be suppressed in a cell by RNA interference (RNAi).

A mutant protein refers to the protein encoded by a gene having a mutation, e.g., a missense or nonsense mutation in the targeted ADNSHL-causing gene product. A mutant ADNSHL-causing gene may be disease-causing, i.e., may lead to a disease associated with the presence of ADNSHL-causing gene product in an animal having either one or two mutant allele(s).

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters. An "allele" is one of several alternative forms of a gene occupying a given locus on a chromosome.

The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

A "nucleotide sequence" is a polymer of DNA or RNA that can be single-stranded or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid nucleic acid molecules and compositions containing those molecules. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

A "variant" or "mutant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

A "transgene" refers to a gene that has been introduced into the genome by transformation. Transgenes include, for example, DNA that is either heterologous or homologous to the DNA of a particular cell to be transformed. Additionally, transgenes may include native genes inserted into a non-native organism, or chimeric genes. The term "endogenous gene" refers to a native gene in its natural location in the genome of an organism.

"Wild-type" refers to the normal gene or organism found in nature.

"Genome" refers to the complete genetic material of an organism.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an miRNA. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence", i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

"Functional RNA" refers to sense RNA, antisense RNA, ribozyme RNA, miRNA, or other RNA that may not be translated but yet has an effect on at least one cellular process.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell.

"cDNA" refers to a single- or double-stranded DNA that is complementary to and derived from mRNA.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted herein, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

The "initiation site" is the position surrounding the first nucleotide that is part of the transcribed sequence, which is also defined as position+1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of miRNA constructs, expression may refer to the transcription of the miRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms. "Antisense inhibition" refers to the production of antisense RNA transcripts capable of suppressing the expression of protein from an endogenous gene or a transgene.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

"Chromosomally-integrated" refers to the integration of a foreign gene or nucleic acid construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., E. coli) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

The miRNAs of the present invention can be generated by any method known to the art, for example, by in vitro transcription, recombinantly, or by synthetic means. In one example, the miRNAs can be generated in vitro by using a recombinant enzyme, such as T7 RNA polymerase, and DNA oligonucleotide templates.

Nucleic Acid Molecules of the Invention

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. The RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild-type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the miRNA, or the like. Such elements may be included in the DNA as desired to obtain the optimal performance of the miRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of $E.$ $coli$ and the luciferase gene from firefly Photinus pyralis. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein.

The recombinant DNA can be readily introduced into the host cells, e.g., mammalian, bacterial, yeast or insect cells by transfection with an expression vector composed of DNA encoding the miRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described herein below, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585,362.

As discussed herein, a "transfected" "or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the miRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

The instant invention provides a cell expression system for expressing exogenous nucleic acid material in a mammalian recipient. The expression system, also referred to as a "genetically modified cell," comprises a cell and an expression vector for expressing the exogenous nucleic acid material. The genetically modified cells are suitable for administration to a mammalian recipient, where they replace the endogenous cells of the recipient. Thus, the preferred genetically modified cells are non-immortalized and are non-tumorigenic.

According to one embodiment, the cells are transfected or otherwise genetically modified ex vivo. The cells are isolated from a mammal (preferably a human), nucleic acid introduced (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

As used herein, "exogenous nucleic acid material" refers to a nucleic acid or an oligonucleotide, either natural or synthetic, which is not naturally found in the cells; or if it is naturally found in the cells, is modified from its original or native form. Thus, "exogenous nucleic acid material" includes, for example, a non-naturally occurring nucleic acid that can be transcribed into an anti-sense RNA, a miRNA, as well as a "heterologous gene" (i.e., a gene encoding a protein that is not expressed or is expressed at biologically insignificant levels in a naturally-occurring cell of the same type). To illustrate, a synthetic or natural gene encoding human erythropoietin (EPO) would be considered "exogenous nucleic acid material" with respect to human peritoneal mesothelial cells since the latter cells do not naturally express EPO. Still another example of "exogenous nucleic acid material" is the introduction of only part of a gene to create a recombinant gene, such as combining an regulatable promoter with an endogenous coding sequence via homologous recombination.

The condition amenable to gene inhibition therapy may be a prophylactic process, i.e., a process for preventing disease or an undesired medical condition. Thus, the instant invention embraces a system for delivering miRNA that has a prophylactic function (i.e., a prophylactic agent) to the mammalian recipient.

Methods for Introducing the Expression Cassettes of the Invention into Cells

The inhibitory nucleic acid material (e.g., an expression cassette encoding miRNA directed to a gene of interest) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including calcium phosphate DNA co-precipitation, DEAE-dextran, electroporation, cationic liposome-mediated transfection, tungsten particle-facilitated microparticle bombardment, and strontium phosphate DNA co-precipitation.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the miRNA together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain an regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of miRNA generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding a miRNA sequence that are in the cell.

In addition to at least one promoter and at least one heterologous nucleic acid sequence encoding the miRNA, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the miRNA(s), the other vector containing a selection gene. The selection of a suitable promoter, enhancer, selection gene, and/or signal sequence is deemed to be within the scope of one of ordinary skill in the art without undue experimentation.

The following discussion is directed to various utilities of the instant invention. For example, the instant invention has utility as an expression system suitable for silencing the expression of gene(s) of interest.

The instant invention also provides methods for genetically modifying cells of a mammalian recipient in vivo. According to one embodiment, the method comprises introducing an expression vector for expressing an miRNA sequence in cells of the mammalian recipient in situ by, for example, injecting the vector into the recipient.

Delivery Vehicles for the Expression Cassettes of the Invention

Delivery of compounds into tissues can be limited by the size and biochemical properties of the compounds. Currently, efficient delivery of compounds into cells in vivo can be achieved only when the molecules are small (usually less than 600 Daltons).

The selection and optimization of a particular expression vector for expressing a specific miRNA in a cell can be accomplished by obtaining the nucleic acid sequence of the miRNA, possibly with one or more appropriate control regions (e.g., promoter, insertion sequence); preparing a vector construct comprising the vector into which is inserted the nucleic acid sequence encoding the miRNA; transfecting or transducing cultured cells in vitro with the vector construct; and determining whether the miRNA is present in the cultured cells.

Vectors for cell gene therapy include viruses, such as replication-deficient viruses (described in detail below). Exemplary viral vectors are derived from Harvey Sarcoma virus, ROUS Sarcoma virus, (MPSV), Moloney murine leukemia virus and DNA viruses (e.g., adenovirus).

Replication-deficient retroviruses are capable of directing synthesis of all virion proteins, but are incapable of making infectious particles. Accordingly, these genetically altered retroviral expression vectors have general utility for high-efficiency transduction of nucleic acid sequences in cultured cells, and specific utility for use in the method of the present invention. Such retroviruses further have utility for the efficient transduction of nucleic acid sequences into cells in vivo. Retroviruses have been used extensively for transferring nucleic acid material into cells. Protocols for producing replication-deficient retroviruses (including the steps of incorporation of exogenous nucleic acid material into a plasmid, transfection of a packaging cell line with plasmid, production of recombinant retroviruses by the packaging cell line, collection of viral particles from tissue culture media, and infection of the target cells with the viral particles) are well known in the art.

An advantage of using retroviruses for gene therapy is that the viruses insert the nucleic acid sequence encoding the miRNA into the host cell genome, thereby permitting the nucleic acid sequence encoding the miRNA to be passed on to the progeny of the cell when it divides. Promoter sequences in the LTR region have can enhance expression of an inserted coding sequence in a variety of cell types. Some disadvantages of using a retrovirus expression vector are (1) insertional mutagenesis, i.e., the insertion of the nucleic acid sequence encoding the miRNA into an undesirable position in the target cell genome which, for example, leads to unregulated cell growth and (2) the need for target cell proliferation in order for the nucleic acid sequence encoding the miRNA carried by the vector to be integrated into the target genome.

Another viral candidate useful as an expression vector for transformation of cells is the adenovirus, a double-stranded DNA virus. The adenovirus is infective in a wide range of cell types, including, for example, muscle and endothelial cells.

Adenoviruses (Ad) are double-stranded linear DNA viruses with a 36 kb genome. Several features of adenovirus have made them useful as transgene delivery vehicles for therapeutic applications, such as facilitating in vivo gene delivery. Recombinant adenovirus vectors have been shown to be capable of efficient in situ gene transfer to parenchymal cells of various organs, including the lung, brain, pancreas, gallbladder, and liver. This has allowed the use of these vectors in methods for treating inherited genetic diseases, such as cystic fibrosis, where vectors may be delivered to a target organ.

Like the retrovirus, the adenovirus genome is adaptable for use as an expression vector for gene therapy, i.e., by removing the genetic information that controls production of the virus itself. Because the adenovirus functions in an extrachromosomal fashion, the recombinant adenovirus does not have the theoretical problem of insertional mutagenesis.

Several approaches traditionally have been used to generate the recombinant adenoviruses. One approach involves direct ligation of restriction endonuclease fragments containing a nucleic acid sequence of interest to portions of the adenoviral genome. Alternatively, the nucleic acid sequence of interest may be inserted into a defective adenovirus by homologous recombination results. The desired recombinants are identified by screening individual plaques generated in a lawn of complementation cells.

Application of miRNA is generally accomplished by transfection of synthetic miRNAs, in vitro synthesized RNAs, or plasmids expressing miRNAs. More recently, viruses have been employed for in vitro studies and to generate transgenic mouse knock-downs of targeted genes. Recombinant adenovirus, adeno-associated virus (AAV) and feline immunodeficiency virus (FIV) can be used to deliver genes in vitro and in vivo. Each has its own advantages and disadvantages. Adenoviruses are double stranded DNA viruses with large genomes (36 kb) and have been engineered by my laboratory and others to accommodate expression cassettes in distinct regions.

Adeno-associated viruses have encapsidated genomes, similar to Ad, but are smaller in size and packaging capacity (~30 nm vs. ~100 nm; packaging limit of ~4.5 kb). AAV contain single stranded DNA genomes of the + or the − strand. Eight serotypes of AAV (1-8) have been studied extensively. An important consideration for the present application is that AAV5 transduces striatal and cortical neurons, and is not associated with any known pathologies.

Adeno associated virus (AAV) is a small nonpathogenic virus of the parvoviridae family. AAV is distinct from the other members of this family by its dependence upon a helper virus for replication. In the absence of a helper virus, AAV may integrate in a locus specific manner into the q arm of chromosome 19. The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosohedral capsid is approximately 20 nm in diameter.

Further provided by this invention are chimeric viruses where AAV can be combined with herpes virus, herpes virus amplicons, baculovirus or other viruses to achieve a desired tropism associated with another virus. For example, the AAV4 ITRs could be inserted in the herpes virus and cells could be infected. Post-infection, the ITRs of AAV4 could be acted on by AAV4 rep provided in the system or in a separate vehicle to rescue AAV4 from the genome. Therefore, the cellular tropism of the herpes simplex virus can be combined with AAV4 rep mediated targeted integration. Other viruses that could be utilized to construct chimeric viruses include lentivirus, retrovirus, pseudotyped retroviral vectors, and adenoviral vectors.

Also provided by this invention are variant AAV vectors. For example, the sequence of a native AAV, can be modified at individual nucleotides. The present invention includes native and mutant AAV vectors. The present invention further includes all AAV serotypes.

FIV is an enveloped virus with a strong safety profile in humans; individuals bitten or scratched by FIV-infected cats do not seroconvert and have not been reported to show any signs of disease. Like AAV, FIV provides lasting transgene expression in mouse and nonhuman primate neurons, and transduction can be directed to different cell types by pseudotyping, the process of exchanging the virus's native envelope for an envelope from another virus.

Thus, as will be apparent to one of ordinary skill in the art, a variety of suitable viral expression vectors are available for transferring exogenous nucleic acid material into cells. The selection of an appropriate expression vector to express a therapeutic agent for a particular condition amenable to gene silencing therapy and the optimization of the conditions for insertion of the selected expression vector into the cell, are within the scope of one of ordinary skill in the art without the need for undue experimentation.

In another embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (Promega®, Madison, Wis.). However, the efficiency of transfection by these methods is highly dependent on the nature of the target cell and accordingly, the conditions for optimal transfection of nucleic acids into cells using the herein-mentioned procedures must be optimized. Such optimization is within the scope of one of ordinary skill in the art without the need for undue experimentation.

Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art. As used herein, the term "therapeutic miRNA" refers to any miRNA that has a beneficial effect on the recipient. Thus, "therapeutic miRNA" embraces both therapeutic and prophylactic miRNA.

Administration of miRNA may be accomplished through the administration of the nucleic acid molecule encoding the miRNA. Pharmaceutical formulations, dosages and routes of administration for nucleic acids are generally known.

The present invention envisions treating ADNSHL in a mammal by the administration of an agent, e.g., a nucleic acid composition, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the inner ear. Alternatively the therapeutic agent may be introduced systemically (e.g., intraveneously). In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0. saline solutions and water.

The invention will now be illustrated by the following non-limiting Examples.

EXAMPLE 1

This invention relates to a method of using allele-specific RNA interference to decrease the rate of hearing loss. The overriding hypothesis is that allele-specific RNAi-mediated gene therapy can prevent progressive Autosomal Dominant Non-Syndromic Hearing Loss (ADNSHL). miRNAs have been identified to selectively knock-down deafness-causing genes (FIG. 1). The miRNAs can be delivered to the inner ear cells a number of different ways, including intravenously and directly into the inner ear.

The process of generating and identifying the relevant miRNA is as follows:
1. Mutation in specific deafness-causing gene is identified,
2. Mutated nucleotide and flanking normal nucleotides on either side of mutated nucleotide is tested as microRNAs for potency to suppress expression of mutant gene (predictions can be made using computer algorithms but in vitro must also be done),
3. The best in vitro miRNA is used to make a mutation-specific miRNA. This miRNA is specific for this particular mutation only, but it will work in all persons with this mutation. This miRNA will NOT work in persons with mutations is other genes or even different mutations in the same gene.

Therefore the treatment is an example of personalized medical therapy for hearing loss. This therapy is specific for autosomal dominant progressive hearing loss. The validity of this approach was demonstrated in mice carrying the identical mutation related to hearing loss—mice were injected and followed for several months.

Figure 2:
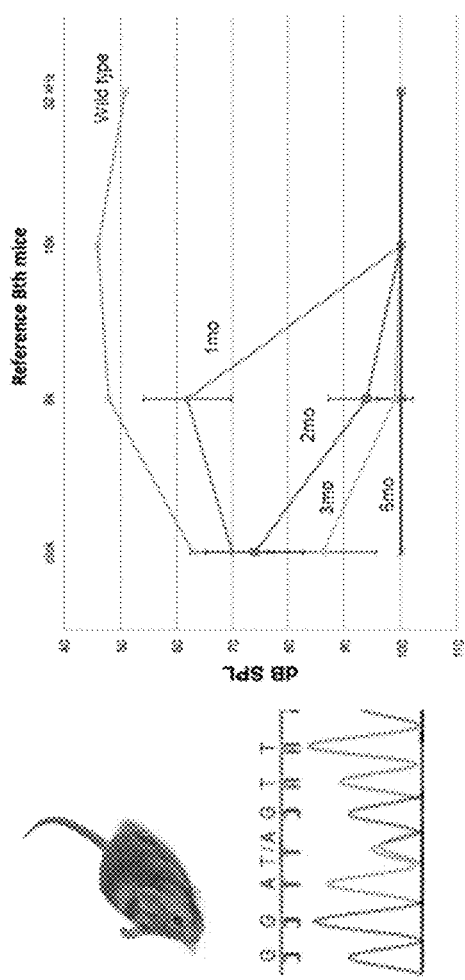
FIG. 2. A mouse carrying a nucleotide change in Tmc1 (M412K) develops progressive hearing loss over time, as demonstrated by the lines representing the hearing of mice at age one month (1 mo), two months, three months and six months, as compared to the normal hearing (wild-type) mouse.
Figure 4:
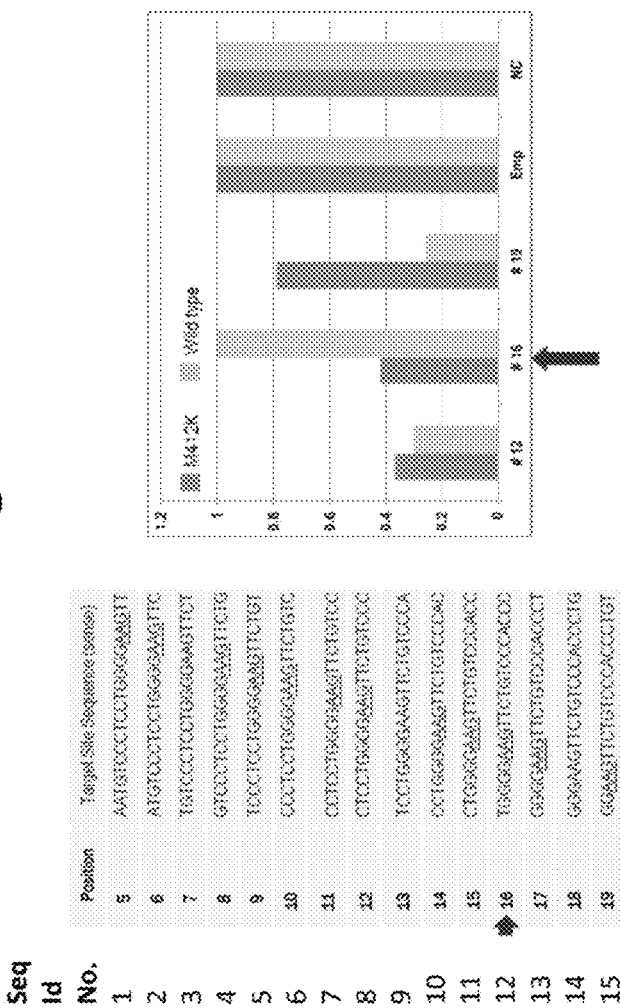
FIG. 4. After identifying a mutation that causes ADN-SHL, multiple miRNAs that target the specific nucleotide change must be made (SEQ ID Nos: 1-15). The location of the mutated nucleotide is changed relative to the complete target site sequence. All miRNAs are tested to determine which miRNA has the greatest potency in knocking down the mutant allele (shown by the dark bars on the left) as compared to the wild-type allele (shown by the light bars on the right). The ideal miRNA will have a dramatic knockdown effect on the mutant allele but no effect on the wild-type allele. Although identifying a 'perfect' miRNA is unlikely, the best miRNA is used to make a therapeutic agent. Of the miRNAs shown on the graph, the miRNA that targets Position #16 (SEQ ID NO:12) is best.
Figure 5:
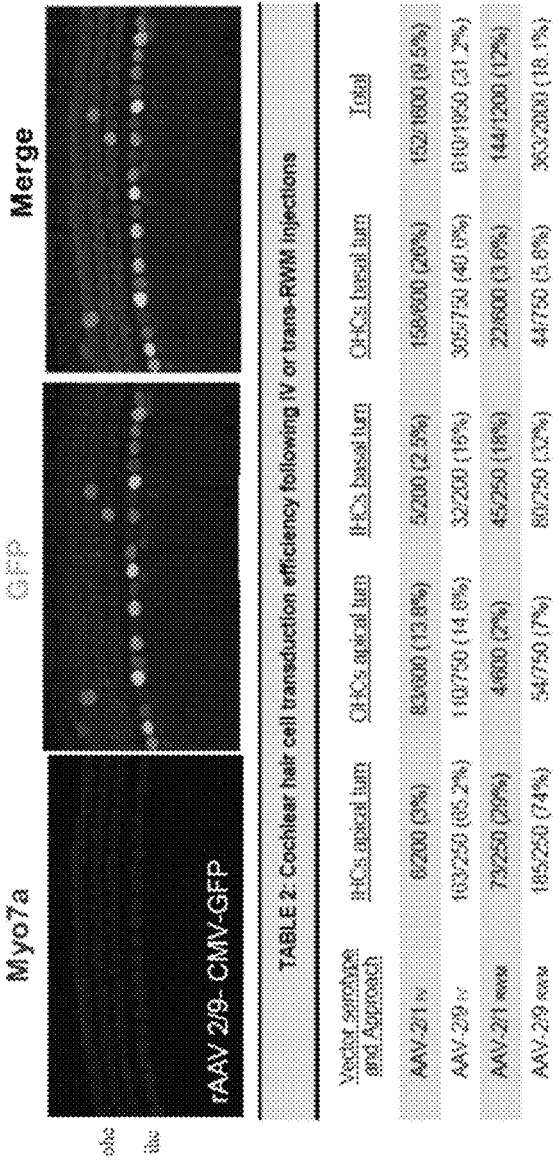
FIG. 5. This figure shows transduction efficiency of inner ear hair cells following introduction of the vector (AAV) using either an intravenous (IV) or trans-round window membrane (RWM) route of delivery. Both inner hair cells (IHCs) and outer hair cells (OHCs) are transduced. The transduction occurs in both the apical and basal turns (that is, throughout the cochlea).

Beethoven (Bth) mice have a missense mutation in Tmc1 (M412K) that leads to hearing loss through a dominant-negative or gain-of-function mechanism (FIG. 2). Mutations of human TMC1 cause autosomal dominant hearing loss at the DFNA36 locus (FIG. 3) (Zhao et al., *PLos One,* 9(5): e97064. doi:10.1371/journal.pone.0097064 (2014)). Vectors encoding miRNAs were identified that selectively knockdown its targeted deafness-causing gene (FIG. 4) (Boudreau, et al., *Methods Enzymol.,* 507:275-296 (2012)). The miRNAs can be delivered to the inner ear cells in a number of different ways, including intravenously and directly into the inner ear, whereby the hair cells are targeted (FIG. 5) (Azaiez et al., *Hum. Mut.,* 35:819-823 (2014); Xia et al., *PLoS ONE,* 7(8): e43218. Doi:10.1371/journal/pone.0043218 (2012)).

Figure 6:
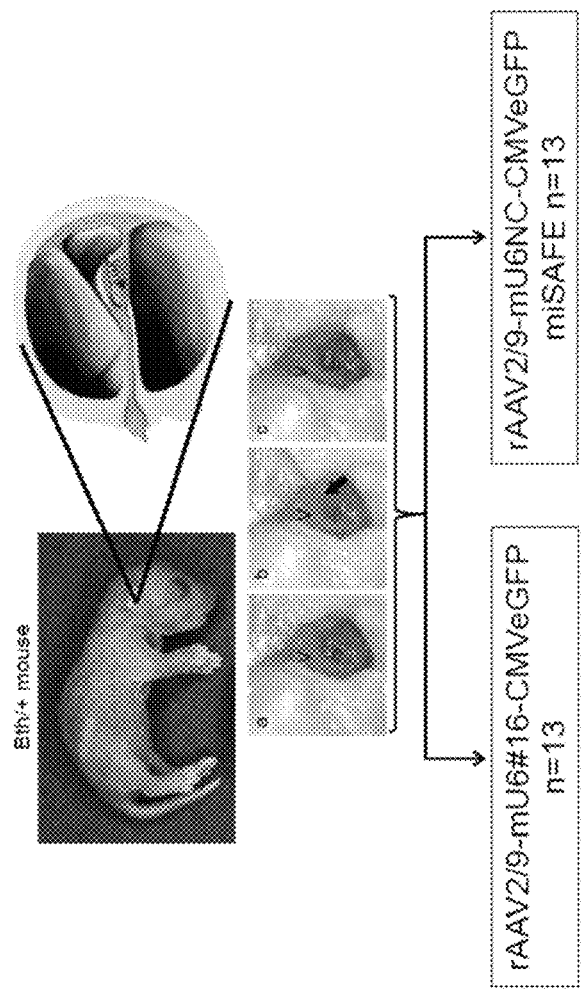
FIG. 6. The experimental method for trans-round window membrane delivery of the therapeutic agent is illustrated. Thirteen animals were treated with the therapeutic agent (miRNA#16) and 13 animals were treated with a control miRNA (miSAFE). miSAFE has no effect on the inner ear and no systemic off-target effects, making it an excellent control miRNA.
Figure 7:
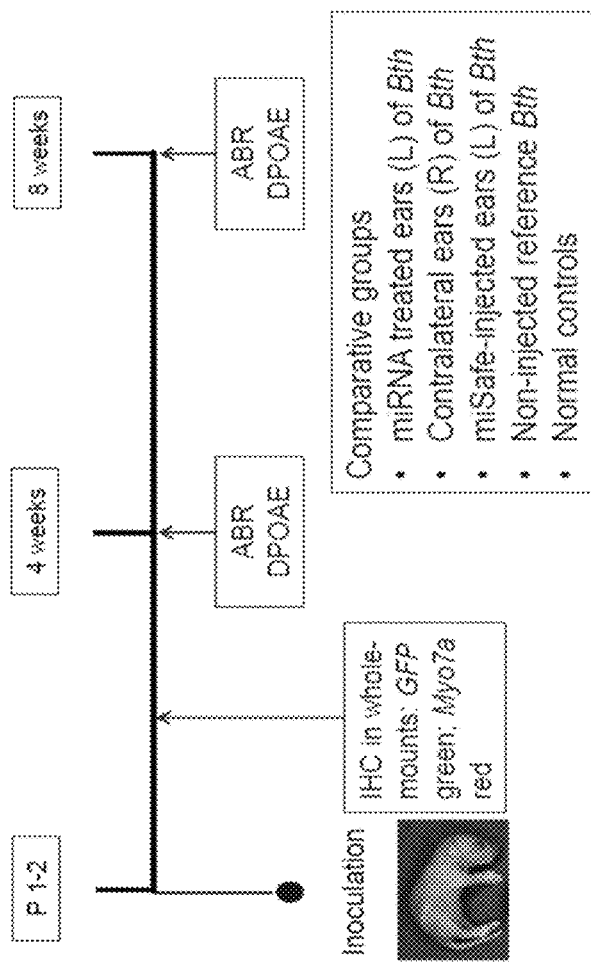
FIG. 7. The experimental timeline is shown. After inoculation, immunohistochemistry was completed at two weeks. Animals were then tested at four week intervals. Hearing was measured by auditory brainstem response (ABR) testing and distortion product otoacoustic emission (DPOAE) testing. Five experimental groups of animals were tested: 1) the miRNA treated animals (left ear); 2) the contralateral ear (right ear) of the same animals; 3) the miSAFE treated ears (left ear); 4) non-treated animals carrying the Tmc1M412K mutation; 5) normal controls.
Figure 8:
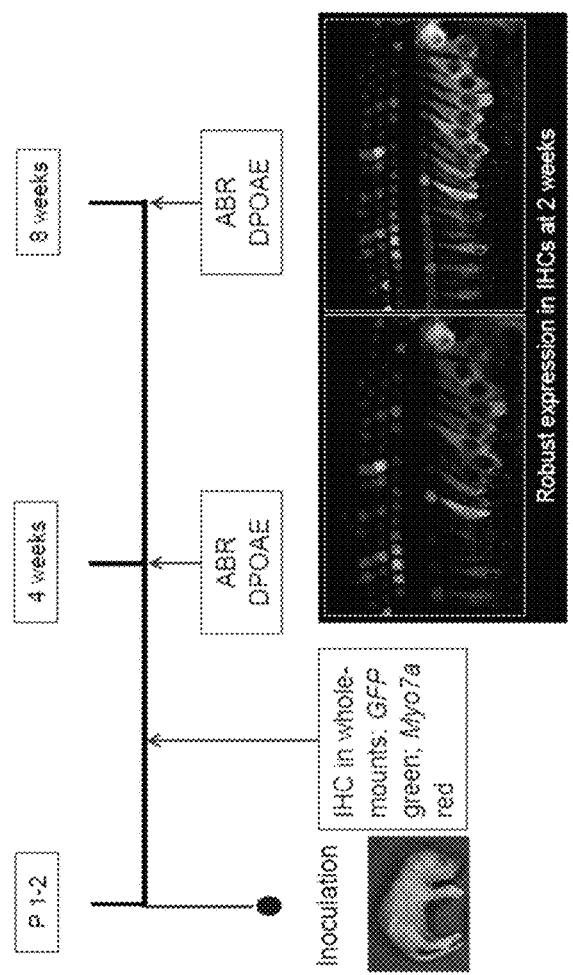
FIG. 8. Robust expression of the delivered therapeutic was apparent by visualization of a reporter gene, GFP, in inner hair cells (bottom) and outer hair cells (top circles). A labeled antibody to Myo7a was used to mark hair cells.
Figure 9:
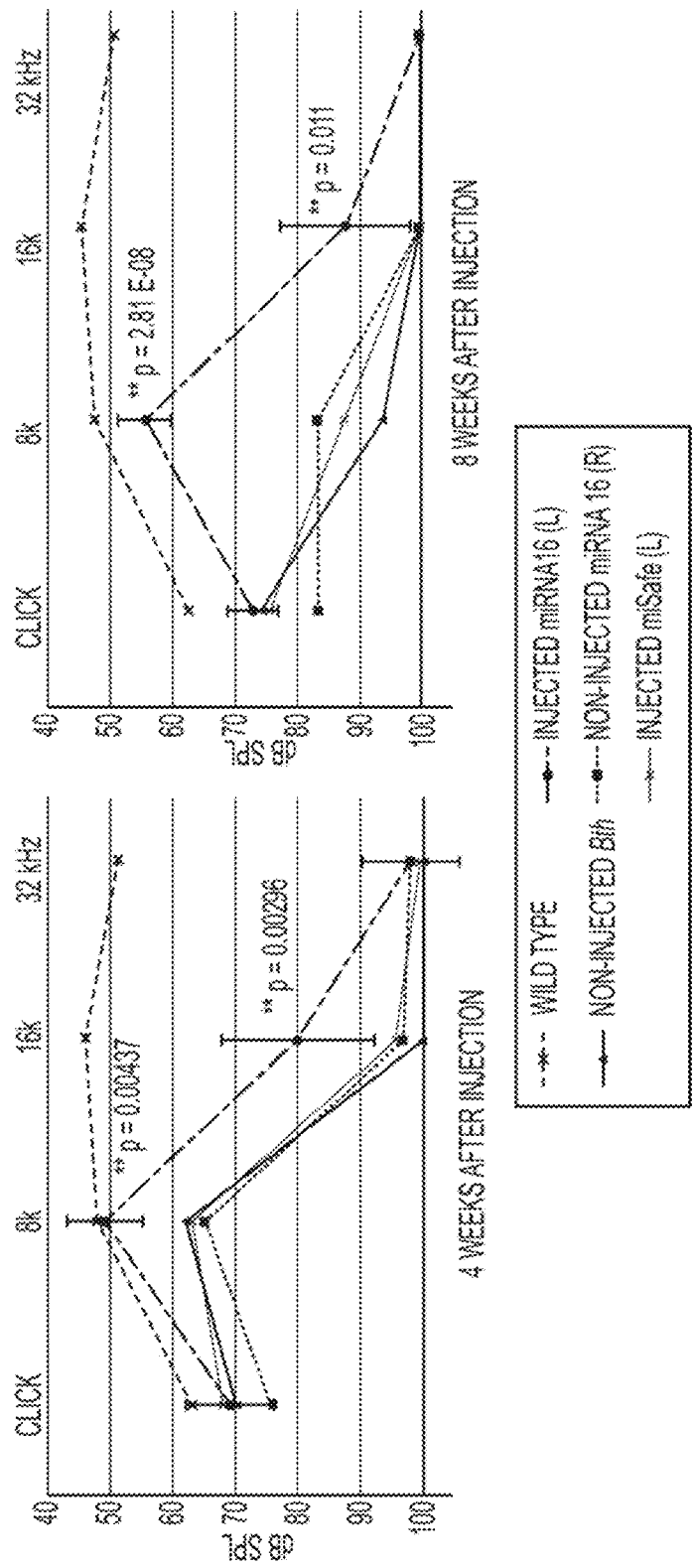
FIG. 9. In treated animals, the rate of hearing loss was markedly decreased. Note particularly at 8 kHz in treated animals at 4 weeks, hearing is equivalent to hearing in wild-type controls. At 8 weeks, there has been a slight decrease in hearing at 8 kHz, but hearing thresholds in treated animals are much better than hearing thresholds in untreated animals or in animals treated with miSAFE.
Figure 10:
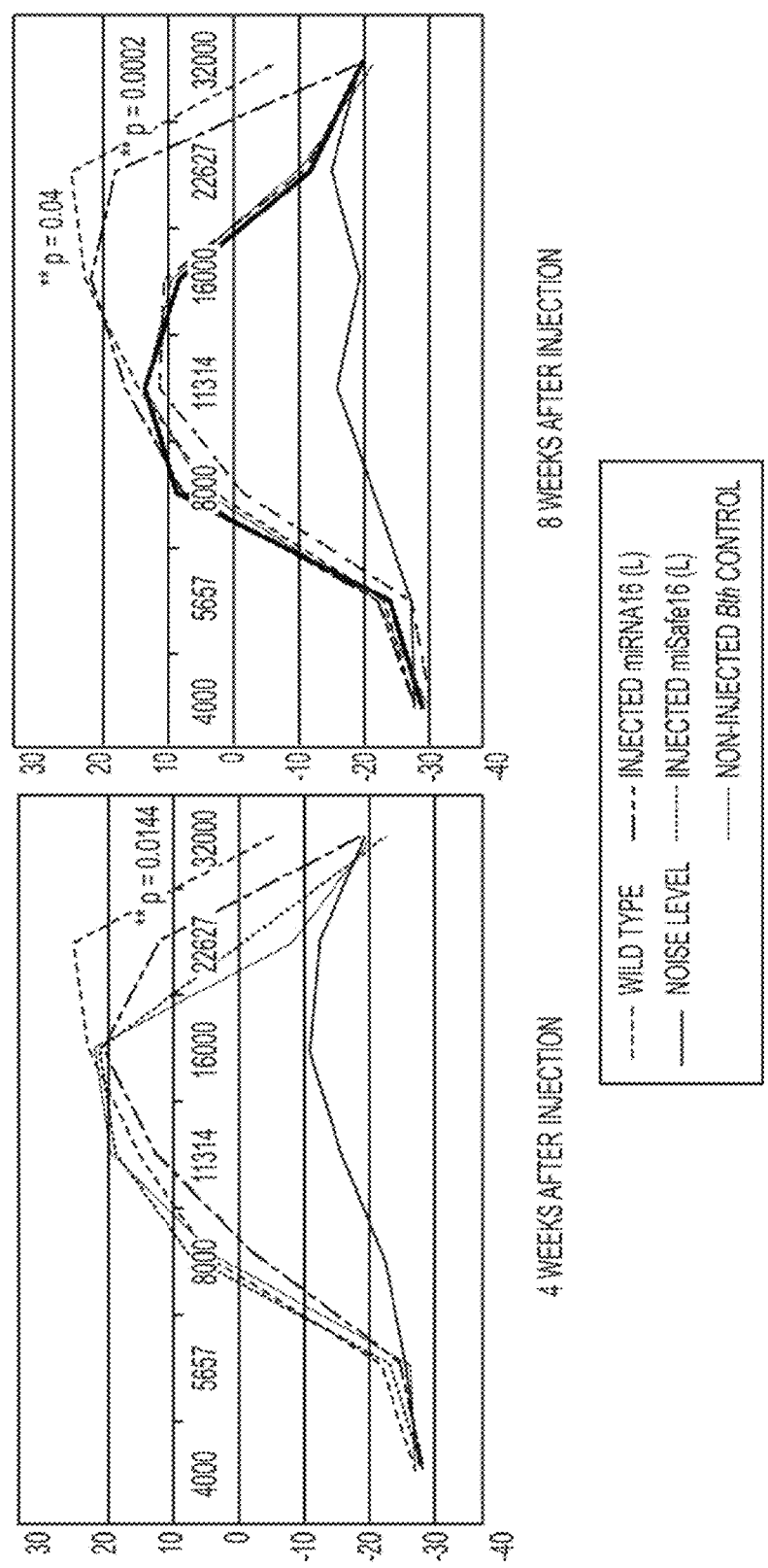
FIG. 10. Results were similar using distortion product otoacoustic emission (DPOAE) testing. Note in particular at 8 weeks the DPOAE similarity between the wild-type and miRNA treated animals, consistent with robust transduction of outer hair cells and preservation of outer hair cell function.

Trans-Round window membrane (trans-RWM) inoculation of 0.5 µl AAV was complete on two experimental groups of P2 mice (FIG. 6) (Boudreau, et al., *Molec. Therapy,* 19(12):2169-2177 (2011). Animals were injected and followed for several months (FIG. 7). Expression of the reporter gene and the therapeutic miRNA in the inner ear was robust (FIG. 8). The amount of hearing loss decreased as demonstrated by ABR (FIG. 9). The amount of hearing loss decreased as demonstrated by DPOAEs (FIG. 10).

The expression of a gene carrying a mutation that causes hearing loss can be decreased by using RNA interference. The decrease in the expression is associated with an improvement in hearing. The methodology is broadly applicable to all forms of dominant hearing loss that are progressive and for which an miRNA can be designed.

EXAMPLE 2

Hearing impairment is the most common sensory deficit, affecting more than 250 million people worldwide and broadly impacting their quality of life. Not only does it limit the ability to interpret speech sounds leading to delayed language acquisition in infancy, but in adulthood hearing impairment can lead to economic disadvantage, social isolation and stigmatization. Current treatment options focus on hearing aids and cochlear implants to bypass the biologic deficit by amplifying sounds (hearing aids) or to encode them as electrical impulses that are transmitted to the auditory nerve by an implanted electrode array (cochlear implant). While these two habilitation options are extremely effective, they do not restore "normal" hearing.

The recent adoption of comprehensive genetic testing platforms in the assessment of hearing impairment has highlighted the extreme heterogeneity of hereditary hearing loss and its broad prevalence. With an overall diagnostic rate of about 40%, after an audiogram these platforms have become the single best test to obtain in the evaluation of hearing loss. The resultant plethora of identified causes of genetic deafness is presaging the development of personalized forms of gene therapy as interventional strategies to prevent hearing loss or restore normalcy. In mouse models of deafness, there has been variable success in preventing abnormal splicing with allelic-specific oligonucleotides in animals models of USH1C and in restoring gene copy number in animals deficient in VGLUT3, TMC1 and WHRN. Our own work has focused on the application of RNA interference (RNAi) to selectively suppress the mutant allele in animal models of autosomal dominant non-syndromic hearing loss (ADNSHL) using an artificial micro-RNA (miRNA) based approach.

Beethoven (Bth), Tmc1 and the p.M412K allele

The Beethoven (Bth) mutant was used for these studies. This mouse segregates the semi-dominant p.M412K allele of Tmc1, which arose in a large scale ENU (N-ethyl-N-nitrosurea) mutagenesis program. Bth/+ mice have progressive hearing loss, with auditory brainstem response (ABR) thresholds affected in a high-to-low-frequency gradient corresponding to a base-to-apex gradient of hair cell degeneration. The encoded protein, Tmc1, is a transmembrane protein that interacts with the tip-link proteins protocadherin 15 and cadherin 23, indicating that Tmc1 plays a role in mechanotransduction. Four mutations have been reported in the human homolog, TMCJ, to cause ADNSHL at the DFNA36 locus. One, p.M418K, is orthologous to the murine p.M412K mutation and segregates in a large Chinese family with post-lingual sensorineural hearing loss. In this kindred, age of onset varies from 5 to 25 years and by the age of 50, hearing thresholds are in the severe-to-profound range across all frequencies.

Hearing loss was sought to be prevented by using an artificial micro-RNA (miRNA) to suppress expression of the mutant p.K412 allele. Multiple small interfering RNAs were tested, incorporating the most specific into the miRNA design. In vitro miRNA screening in COS-7 cells showed potent and allele-specific expression of one miRNA, which was cloned into recombinant AAV serotype 2/9 (rAAV2/9) as a dual transgene cassette of mouse U6-driven miRNA targeting p.M412K coupled up-stream of CMV-driven eGFP (rAAV2/9miTmck412.16eGFP). A control vector was designed carrying a U6-driven scrambled sequence (aka miSafe) and CMV-driven eGFP (rAAV2/9miSafeGFP).

This potential therapeutic was delivered to murine inner ears using a trans-round-window-membrane (trans-RWM) approach. Surgery was performed on mice at P1-2 under hypothermic anesthesia using an operating microscope to visualize the bulla, which was accessed through a post-auricular incision. After entering the middle ear space, ~0.5 μl of a 10:1 viral vector (rAAA2/9miTmc1k412.16eGFP or control):2.5% fast green dye mix was injected into the left ear of each mouse. Robust in vivo expression was confirmed by comparing left and right *cochleae* harvested from Bth/+ P1-2 injected mice 2 and 4 weeks after transfection.

Auditory Testing

To determine whether auditory function was impacted, hearing thresholds were measured as auditory brainstem responses (ABRs) and distortion product otoacoustic emissions (DPOAEs) in four groups of mice: 1) wild-type littermates (2 mo: n=3; 6 mo: n=5; C3H4/FeJ inbred mice); 2) Bth/+ noninjected mice (1 mo: n=5; 2 mo: n=4; 3 mo: n=5; 6 mo: n=3); 3) Bth/+rAAV2/9 miSafe GFP injected control mice (Bth/+miSafe; n=13); and, 4) Bth/+rAAA2/9miTmc1k412.16eGFP injected mice (Bth/+miTmc; n=10). ABR thresholds were assessed as both click and 5 ms pure-tones responses at 8 kHz, 16 kHz and 32 kHz, while DPOAEs were measured using frequency glides, as described (Soken, Laryngoscope. 2013 December; 123(12): E109-15).

Figure 11:
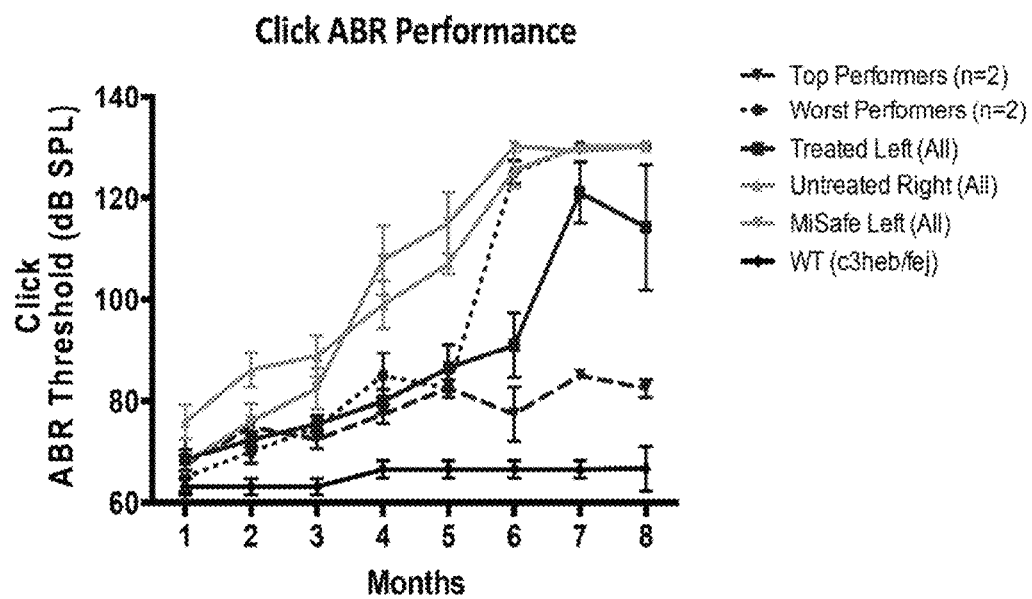
FIG. 11. Hearing loss progression in Bth/+ mice is attenuated by miRNA treatment. The left ears of Bth/+miTmc treated mice show slower progression of hearing loss over time as measured by click ABRs. Note that in the top two performers, hearing is stable after 3 months and is unchanged at 8 months. The worst two performers, in comparison, have rapidly progressive hearing loss after 20 weeks, ultimately having thresholds indistinguishable from Bth/+ animals and Bth/+miSafe injected left ears. As a group, however, all Bth/+miTmc1 treated mice had significant protection against hearing loss for 20 weeks.

Click ABRs cover a broad frequency and stimulus range (2 kHz-8 kHz and up to 130 dB SPL). By testing animals every 4 weeks for 32 weeks, mouse the progressive deterioration of hearing thresholds were documented in Bth/+, which fell to the severe-to-profound level by 5 to 6 months of age, consistent with earlier reports. The progression of hearing loss was similar in the untreated right ears of Bth/+miTmc mice and in the injected left ears of Bth/+ miSafe mice, suggesting that the viral inoculation procedure and the vector itself had little negative impact on auditory function and did not contribute to the decline in hearing thresholds. In contrast, the progression of hearing loss was slower in the injected left ears of Bth/+miTmc mice, with the difference through 16 to 24 weeks being significant as a group compared to controls. At 28 weeks, there was a marked drop in ABR thresholds in the Bth/+miTmc treated mice. By looking at outliers (the two best and the two worst performing animals), it was found that while the two worst performers showed hearing protection up to 20 weeks, there was complete loss of hearing protection by 24 weeks. In contrast, throughout the 32 weeks study period, the two top performers had stable hearing thresholds that were 15 to 20 dB above the thresholds of wild type C3heb/Fej litter-mate controls. The maximal level of hearing protection in these mice is therefore at least 50 dB as compared to the untreated Bth/+ animals after 24 weeks. These data confirm that artificial miRNA gene therapy is viable up to 32 weeks after inoculation, although the extent of treatment efficacy is variable across animals (FIG. 11).

Pure tone ABRs were obtained to measure frequency-specific effects. Bth/+ and Bth/+miSafe mice both showed abnormal or absent hearing at 16 kHz and 32 kHz, consistent with earlier reports (Vreugde, Marcotti). At 8 kHz, hearing loss progressed and by 3 months ABR responses were >100 dB. The rate of progression was not increased in Bth/+miSafe injected mice supporting the nontraumatic nature of the trans-RWM injection at P1-2. In the left ears of Bth/+miTmc mice, 1 month after treatment there was significant preservation of hearing at 8 kHz and 16 kHz, although there was no protective effect at 32 kHz. At 16 kHz the protective effect was lost by 3 months, however at 8 kHz, a protective effect was seen even at 12 weeks. In the two top performers, hearing was preserved at 8 kHz throughout the entire study period (dashed blue line), although at the conclusion of the study hearing thresholds were mildly elevated as compared to wild type littermate controls (solid black line) (FIG. 12). Wave I amplitudes were also measured at 8 kHz at 1 month using Matlab software to calculate peak-to-nadir distance. While the treated left ears in Bth/+miTmc mice had smaller amplitudes overall as compared to wild-type littermate controls, wave I amplitudes were even smaller in untreated control Bth/+ mice. Amplitudes in untreated Bth/+ mice continued to dampen, although in the Bth/+miTmc mice they did not. Wave I latencies were also recorded however there was no significant difference between Bth/+ and Bth/+miTmc mice, both of which had longer latencies that wild-type controls (FIG. 12).

Figure 13:
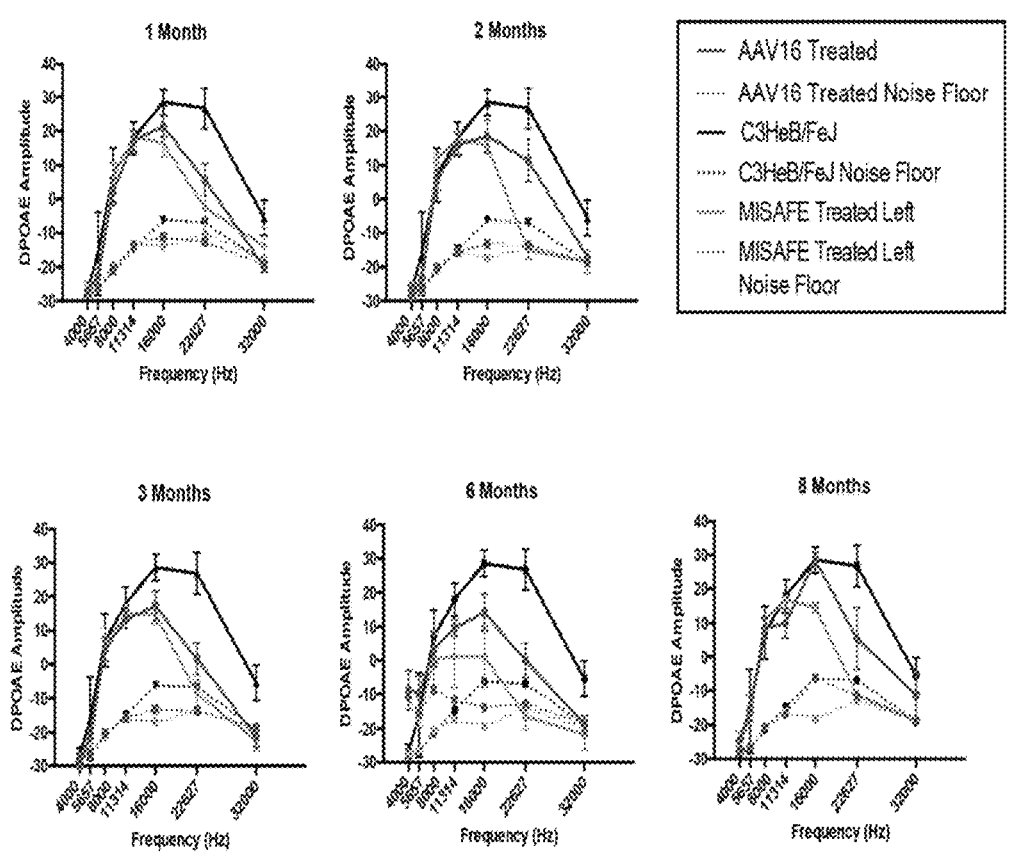
FIG. 13. Distortion-product otoacoustic emission (DPOAE) thresholds. DPOAE amplitudes were measured at 1, 2, 3, 6 and 8 months. Mean DPOAE amplitudes for each animal group are graphed with error bars representing ±standard error of the mean (SEM). Note that in the Bth/+miTmc mice as compared to the Bth/+miSafe mice, DPOAEs are better preserved in the ultra-high frequencies, suggests better OHC survival in the Bth/+miTmc mice in the lower turns of the cochlea.

DPOAEs are an objective measure of outer hair cell (OHC) function and were recorded at the same time points as the ABRs. Consistent with prior reports, DPOAEs were found to be comparable between Bth/+ mice and wild-type controls, reflecting a high degree of OHCs preservation. However, in the ultra-high frequencies from 22 kHz to 32 kHz, a DPOAE decline in Bth/+ mice was identified (data not shown). In both Bth/+miTmc mice and Bth/+miSafe mice, there was no difference in DPOAEs at 1 month, however at 2 months DPOAEs in Bth/+miTmc mice were maintained while in Bth/+miSafe mice there was a sharp decline at 22 kHz and 32 kHz. The difference between Bth/+miTmc mice and Bth/+miSafe mice at 16 kHz and higher persisted over time suggesting greater preservation of OHCs in the basal turn of the cochlea (FIG. 13).

Hair Cell Survival

Figure 15A:
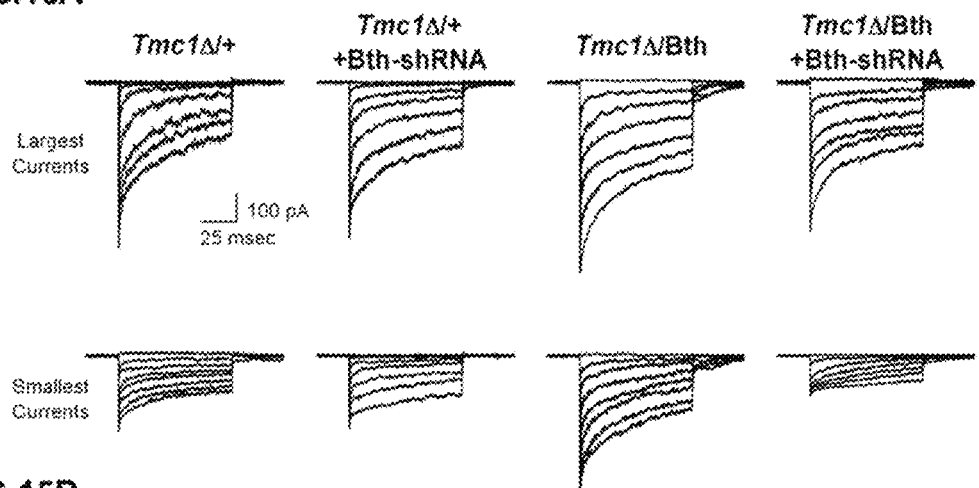
FIGS. 15A-B. Transduction current function is improved with AAVshRNATmc.
Figure 15B:
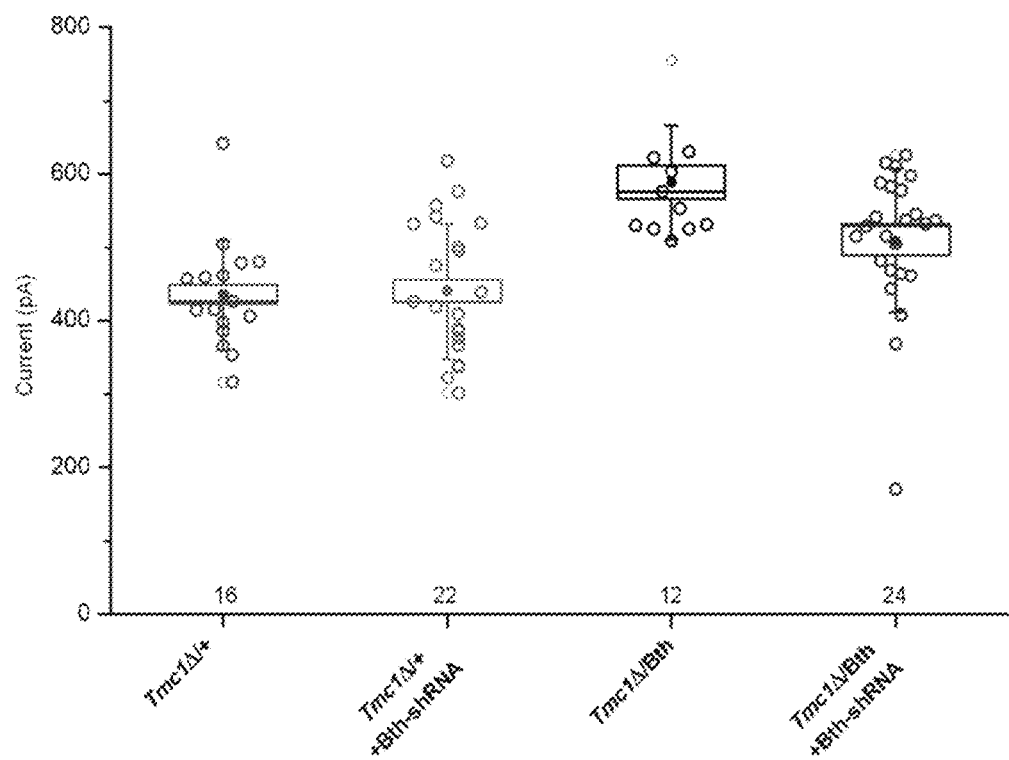

The histological correlate of auditory function in Bth/+ mice is hair cell survival, which was quantitated using immunofluorescence to count hair cells in the four cohorts of animals at either 7 or 8 months. Distance from the apex was measured in 0.25 mm segments using whole mount preparations of *cochleae* and in each segment, IHCs and OHCs were counted using ImageJ Cell Counter software, omitting from the analysis any segments that contained dissection-related damage. As expected, there was near complete IHC and OHC survival in 8-month-old C3HeB/FeJ control animals and a dramatic loss of IHCs (with less OHC loss) in Bth/+ mice in a base-to-apex gradient. Counts in all Bth/+ miSafe-treated left ears were indistinguishable from Bth/+ mice. In Bth/+miTmc mice, in contrast, hair cell survival was markedly different. IHC counts in Bth/+miTmc mice were greatest in the apical region of the cochleae, with visible gaps occurring in the mid-modiolar region that showed inter-animal variability. From the lower mid-modiolar to basal region, Bth/+miTmc mice had a pattern of IHC loss indistinguishable from Bth/+ and Bth/+miSafe mice. There was no improvement in OHC survival in Bth/+miTmc mice as compared to Bth/+ and Bth/+miSafe animals (FIG. 14). Interestingly, only a slight difference in hair cell survival was observed between the mean for the entire Bth/+miTmc cohort as compared to the two best performers, which had ABR thresholds of 75 dB at the conclusion of the study. This finding suggests that while hair cell survival is required, it alone is not sufficient for hearing function in Bth/+ mice. Stereocilia bundles in surviving hair cells were also investigated in both Bth/+miTmc and untreated ears (FIG. 15). Since neither stereocilia nor hair cells themselves were completely absent in profoundly deaf Bth/+ mice, a defect at the molecular level sufficient to compromise auditory acuity likely precedes the anatomic changes we observed.

Mechanotransduction

Tmc1 affects the permeation properties of sensory transduction channels in auditory hair cells and with its closely related ortholog, Tmc2, is a likely component of the mechanotransduction channel. To test the effect of RNA interference and allele specific suppression on channel permeation, transduction currents were measured 8-10 days after exposing IHCs to AAVshRNATmc. Mice were recorded on a Tmc2−/− background to ensure that observed currents were only due to expression of Tmc1, and compared Bth/− mice (mice carrying only one Tmc allele, the mutant p.K412 allele) to Tmc+/− mice (mice carrying only one Tmc allele, the wild-type p.M412 allele) before and after AAV-shRNATmc exposure. As expected, AAVshRNATmc had no effect on currents observed in Tmc+/− mice. Bth/− mice had larger currents that Tmc+/− mice. When exposed to AAVshRNATmc, reduced amplitudes were observed in some Bth/− cells consistent with AAVshRNATmc-mediated restoration of channel permeation (FIG. 15).

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating autosomal dominant non-syndromic hearing loss (ADNSHL) in a patient in need thereof comprising:
   (a) identifying a mutation in an ADNSHL-causing gene, wherein the mutation causes ADNSHL in the patient;
   (b) preparing a ADNSHL therapeutic miRNA, wherein the ADNSHL therapeutic miRNA is of 18 to 25 nucleotides in length and suppresses expression of the ADNSHL-causing gene to a greater level than it suppresses expression of a corresponding wild-type gene; and
   (c) administering to the patient a pharmaceutical composition comprising the ADNSHL therapeutic miRNA and a pharmaceutically acceptable carrier,
      wherein the ADNSHL-causing gene is ACTG1, CCDC50, CEACAM1, COCH, COL11A2, CRYM, DFNA5, DIABLO, DIAPH1, DSPP, EYA4, GJB2, GJB3, GJB6, GRHL2, HOMER2, KCNQ4, MYH14, MYH9, MYO6, P2RX POU4F3, SLC1748, TBC1D24, TECTA, TJP2, TMC1, TNC, or WFS1.

2. The method of claim 1, wherein the ADNSHL-causing gene is TMC1.

3. The method of claim 2, wherein the ADNSHL-causing gene is TMC1 containing a missense mutation M418K.

4. A method of treating autosomal dominant non-syndromic hearing loss (ADNSHL) in a patient in need thereof comprising administering to a patient identified as having a mutation in an ADNSHL-causing gene a pharmaceutical composition comprising pharmaceutically acceptable carrier and a ADNSHL therapeutic miRNA, wherein the miRNA is of 18 to 25 nucleotides in length and suppresses expression of the ADNSHL-causing gene to a greater level than it suppresses expression of a corresponding wild-type gene, wherein the ADNSHL-causing gene is ACTG1, CCDC50, CEACAM1, COCH, COL11A2, CRYM, DFNA5, DIABLO, DIAPH1, DSPP, EYA4, GJB2, GJB3, GJB6, GRHL2, HOMER2, KCNQ4, MYH14, MYH9, MYO6, P2RX, POU4F3, SLC1748, TBC1D24, TECTA, TJP2, TMC1, TNC, or WFS1.

5. The method of claim 4, wherein the miRNA is of 20 to 22 nucleotides in length.

6. The method of claim 4, wherein the miRNA is 21 nucleotides in length.

7. The method of claim 4, wherein the miRNA suppresses the expression of the ADNSHL-causing gene by at least 50% more than it suppresses the expression of the corresponding wild-type gene.

8. The method of claim 4, wherein the pharmaceutical composition further comprises an shRNA or siRNA.

9. The method of claim 4, wherein the miRNA is contained in an expression cassette comprising a promoter operably linked to a nucleic acid encoding the miRNA.

10. The method of claim 9, wherein the promoter is a polII or polIII promoter.

11. The method of claim 9, wherein the promoter is an H1 or U6 promoter.

12. The method of claim 9, wherein the promoter is a tissue-specific promoter.

13. The method of claim 9, wherein the promoter is an inducible promoter.

14. The method of claim 9, wherein the expression cassette further comprises a marker gene.

15. The method of claim 14, wherein the marker gene is green fluorescent protein (GFP).

16. The method of claim 9, wherein the expression cassette is contained in a vector.

17. The method of claim 16, wherein the vector is an adeno-associated virus (AAV) vector, adenovirus vector or bovine AAV vector.

18. The method of claim 17, wherein the pharmaceutical composition is administered intravenously and/or directly into the patient's inner ear.

19. A method of treating autosomal dominant non-syndromic hearing loss (ADNSHL) in a patient in need thereof comprising administering to a patient identified as having a missense mutation in TMC1 (M418K) a pharmaceutical composition comprising pharmaceutically acceptable carrier and a ADNSHL therapeutic miRNA, wherein the miRNA is of 18 to 25 nucleotides in length and suppresses expression of the TMC1 (M418K) gene to a greater level than it suppresses expression of a corresponding wild-type TMC1 gene, wherein the therapeutic miRNA has at least 90% complementarity to any one of SEQ ID NO: 1-15.

20. The method of claim 4, wherein the ADNSHL-causing gene is TMC1.

* * * * *

SEQUENCE LISTING

```
<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aatgtccctc ctggggaagt t                                              21

<210> SEQ ID NO 2
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 2
atgtccctcc tgggaagtt c                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tgtccctcct ggggaagttc t                                             21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtccctcctg gggaagttct g                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tccctcctgg ggaagttctg t                                             21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccctcctggg gaagttctgt c                                             21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cctcctgggg aagttctgtc c                                             21

<210> SEQ ID NO 8
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 8
ctcctgggga agttctgtcc c                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tcctggggaa gttctgtccc a                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cctggggaag ttctgtccca c                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctggggaagt tctgtcccac c                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tggggaagtt ctgtcccacc c                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggggaagttc tgtcccaccc t                                              21

<210> SEQ ID NO 14
<211> LENGTH: 21
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 14
gggaagttct gtcccaccct g                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ggaagttctg tcccaccctg t                                              21
```